(12) United States Patent
Paganelli et al.

(10) Patent No.: US 7,390,828 B2
(45) Date of Patent: Jun. 24, 2008

(54) AMINODERIVATIVES OF BIOTIN AND THEIR CONJUGATES WITH MACROCYCLIC CHELATING AGENTS

(75) Inventors: Giovanni Paganelli, Milan (IT); Marco Chinol, Milan (IT); Mauro Ginanneschi, Florence (IT)

(73) Assignee: Sigma-Tau Industrie Farmaceutiche Riunite S.p.A., Rome (IT)

(*) Notice: Subject to any disclaimer, the term of this patent is extended or adjusted under 35 U.S.C. 154(b) by 396 days.

(21) Appl. No.: 10/468,075

(22) PCT Filed: Feb. 15, 2002

(86) PCT No.: PCT/IT02/00091

§ 371 (c)(1),
(2), (4) Date: Sep. 30, 2003

(87) PCT Pub. No.: WO02/066075

PCT Pub. Date: Aug. 29, 2002

(65) Prior Publication Data

US 2004/0067199 A1 Apr. 8, 2004

(30) Foreign Application Priority Data

Feb. 16, 2001 (IT) .......................... RM2001A0079

(51) Int. Cl.
*A61K 51/04* (2006.01)
*C07D 257/00* (2006.01)
(52) U.S. Cl. ....................... 514/387; 540/474
(58) Field of Classification Search ................. 514/387; 540/474
See application file for complete search history.

(56) References Cited

U.S. PATENT DOCUMENTS

| | | | |
|---|---|---|---|
| 5,283,342 A | 2/1994 | Gustavson et al. | 548/304.1 |
| 5,541,287 A * | 7/1996 | Yau et al. | 530/317 |
| 5,578,287 A * | 11/1996 | Theodore et al. | 424/1.49 |
| 5,608,060 A | 3/1997 | Axworthy et al. | 540/474 |
| 5,616,690 A * | 4/1997 | Axworthy et al. | 530/363 |
| 5,624,896 A * | 4/1997 | Axworthy et al. | 514/8 |
| 5,630,996 A * | 5/1997 | Reno et al. | 424/1.49 |
| 5,847,121 A * | 12/1998 | Yau et al. | 540/474 |
| 5,911,969 A * | 6/1999 | Axworthy et al. | 424/1.11 |
| 5,914,312 A * | 6/1999 | Axworthy et al. | 514/8 |
| 5,955,605 A | 9/1999 | Axworthy et al. | 540/474 |
| 5,968,405 A | 10/1999 | Yamasaki et al. | 252/62.64 |
| 5,976,535 A * | 11/1999 | Fritzberg et al. | 424/182.1 |
| 6,075,010 A * | 6/2000 | Theodore et al. | 514/23 |
| 6,217,869 B1 * | 4/2001 | Meyer et al. | 424/178.1 |
| 6,287,536 B1 * | 9/2001 | Reno et al. | 424/1.49 |
| 6,416,738 B1 * | 7/2002 | Theodore et al. | 424/9.2 |
| 2002/0015705 A1 * | 2/2002 | Theodore et al. | 424/178.1 |
| 2002/0034511 A1 * | 3/2002 | Reno et al. | 424/178.1 |

FOREIGN PATENT DOCUMENTS

| | | | |
|---|---|---|---|
| EP | 0 496 074 | | 7/1992 |
| EP | 1 138 334 A | * | 10/2001 |
| WO | WO 88/08422 A | * | 11/1988 |
| WO | WO 93/25240 A | * | 12/1993 |
| WO | WO 95/14493 A | * | 6/1995 |
| WO | WO 97/10854 A | * | 3/1997 |

OTHER PUBLICATIONS

Wilbur et al., "Biotin Reagents for Antibody Pretargeting. 4. Selection of Biotin Conjugates for in Vivo Application Based on Their Dissociation Rate from Avidin and Streptavidin," Bioconjugate Chem. 2000, 11, pp. 569-583.
Renn et al., "New Approaches to Delivering Metal-Labeled Antibodies to Tumors: Synthesis and Characterization of new Biotinyl Chelate Conjugates for Pre-Targeted Diagnosis and Therapy," Journal of Controlled Release, 39 (1996), pp. 239-249.
Wilbur et al., "Trifunctional Biotinylation Reagents Which Contain a Radiometal Binding Chelate and an Isothiocyanate Group for Conjugation with Biomolecules," J. Labelled Cpd. Radiopharm, 44, Suppl. (2001), pp. S741-S743.
Paganelli et al, "Antibody-guided three-step therapy for high grade glioma with yttrium-90 biotin", European Journal of Nuclear Medicine, vol. 26, No. 4, Apr. 1999, pp. 348-357; XP008019281.

* cited by examiner

*Primary Examiner*—Brenda L Coleman
(74) *Attorney, Agent, or Firm*—Nixon & Vanderhye P.C.

(57) ABSTRACT

Formula (I) compounds are described where the groups are as defined here below, processes for their preparation, and their uses for the preparation of conjugates with radionuclides for use in human and animal therapy and diagnostics, particularly for the diagnosis and therapy of pathological conditions such as tumours (I)

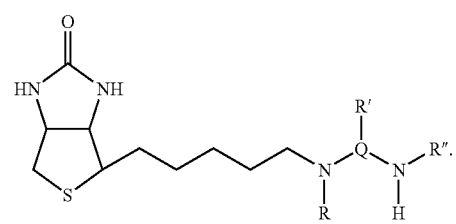

2 Claims, No Drawings

AMINODERIVATIVES OF BIOTIN AND THEIR CONJUGATES WITH MACROCYCLIC CHELATING AGENTS

This application is the U.S. national phase of international application PCT/IT02/00091, filed Feb. 15, 2002, which designated the U.S.

TECHNICAL FIELD

The invention described herein relates to modified biotins useful for the preparation of conjugates with radionuclides for use in human and animal diagnostics and therapy, particularly for the diagnosis and treatment of pathological conditions such as tumours.

The invention described herein relates to the technical field of the preparation of medicaments.

The invention described herein furnishes compounds, methods for their preparation, methods for their use and compositions containing them, which are suitable for industrial application in the pharmaceutical field.

The invention described herein furnishes compounds, compositions and methods suitable for the delivery and release of substances useful in diagnostic and therapeutic medicine and in the treatment of pathological disorders of organs and tissues.

In particular, though not exclusively, the invention described herein relates to the field of anticancer radiopharmaceuticals, meaning both substances which are useful for diagnostic purposes and substances which are useful for cancer prevention and therapy.

BACKGROUND OF THE INVENTION

Tumour therapy is mostly implemented through the use of substances targeted at destroying cancer cells. This can be achieved with cytotoxic substances, which have to penetrate into the tumour cells in order to exert their full effect, or by means of treatment of the tumour cells with radiation of sufficient energy to kill the cells. In both cases there is the problem of delivering the substance in as selective a manner as possible to the target cells, so as to avoid possible damage to the surrounding healthy cells. In the case of radiopharmaceuticals, i.e. substances carrying radioactive portions, the problem of selectively delivering the active part (that is, the radioactive portion) to the tumour target, avoiding as far as possible diffusion of the radionuclide in the body or interaction with healthy cells surrounding the tumour, is perceived as being particularly important.

For a discussion of all the issues involved and the solutions proposed to date, the reader is referred to U.S. Pat. Nos. 5,283,342, 5,608,060 and 5,955,605, assigned to Neorex, and based on a patent application filed on Jun. 9, 1992. These patents are specifically incorporated herein for reference purposes.

In these documents, the problem, amongst others, of the resistance of the molecule carrying the radionuclide to the metabolic attacks of the body is discussed. Specifically, the case accorded most attention is the molecule of biotin, which is one of the first choices for delivering the radionuclide to the tumour cells, thanks to its well-known interaction with avidins. Biotin, as we know from consolidated practice, is bound to the radionuclide-chelating portion, e.g. a molecule of DOTA, via a linker. In fact, the Neorex patents pose the problem of the resistance of the complex consisting of the biotin molecule, as connected to the radionuclide via the linker, to biotinidases, enzymes that break the peptide bond present in the complex. This bond stems from the union of the chelating agent and biotin.

Among its much desired characteristics, the molecule must be eliminated from the body rapidly and efficiently and must be sufficiently small (m.w.<1000) to allow easy distribution into the extracellular fluid where it will bind with the tumour. In addition, it must show proven stability in vivo with only minimal uptake by non-tumour cells and rapid (renal) clearance and must not be metabolised.

To these characteristics one should add the need for a certain amount of stability between the biotin part and the chelating portion of the molecule.

In fact, the chelating portion must not be released in vivo, freeing parts of the molecule, which are potentially dangerous for the body. Experts in the field are clearly familiar with the problem of the release of radionuclide by the chelating portion, including metal ions which are entirely foreign to the body, which may be endowed with radioactivity of various types and even high-energy radiation, which is therefore highly damaging.

SUMMARY OF THE INVENTION

It has now been found that the formula (I) compound, as represented here below, not only fulfills the requisites for such a compound in the therapy and diagnosis of tumours or other diseases which can be detected and treated with compounds of this type, but also presents the advantage of not undergoing metabolic reactions capable of releasing the complexing part of the molecule. In this way, the molecule will be completely eliminated by the body in unaltered form, thus avoiding the problem of the possible release of the chelating part, containing the metal ions imprisoned within it.

One of the objects of the invention described herein is therefore a formula (I) compound:

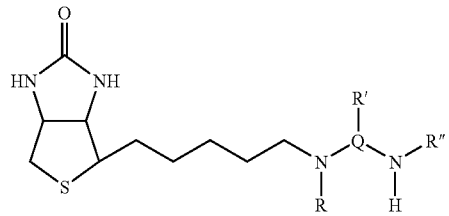

where:

Q is a —$(CH_2)_n$— group, in which n is an integer from 4 to 12, in which case R' does not exist, or Q is selected from the group consisting of —$(CH_2)_a$—CH(R')—$(CH_2)_b$—, where a and b are, independently, integers from 0 to n, and R' is defined here below, or Q is cyclohexyl, phenyl, in which case R' is a substitute on the cyclohexyl or phenyl ring;

R is hydrogen or -Λ, where -Λ is a formula (II) macrocycle:

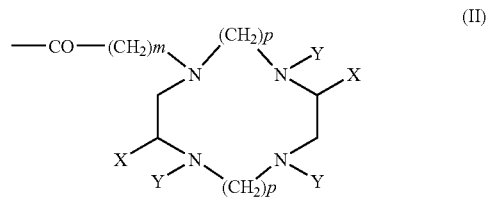

where the various Ys, which may be the same or different, are selected from the group consisting of hydrogen, straight or branched $C_1$-$C_4$ alkyl, —$(CH_2)_m$—COOH, where m is an integer from 1 to 3; X is hydrogen, or the —$CH_2$—U group, where U is selected from methyl, ethyl, p-aminophenyl, or X is the —$(CHW)_o$—Z group, where o is an integer from 1 to 5, W is hydrogen, methyl or ethyl, Z is a heterocyclic group with 5 or 6 members containing one or more heteroatoms selected from O, N—$R_1$, $R_1$ being a hydrogen atom or a straight or branched $C_1$-$C_4$ alkyl group, and S; or Z is selected from —$NH_2$, —NH—C(=NH)—$NH_2$, or —S—$R_2$ where $R_2$ is a straight or branched $C_1$-$C_4$ alkyl group;

p is the integer 2 or 3

R' is selected from the group consisting of hydrogen, straight or branched $C_1$-$C_4$ alkyl, —$(CH_2)_q$-T, where T is selected from the group consisting of S—$CH_3$, —OH, or —COOH, and q is the integer 1 or 2;

R" has the same meanings as R, with the following conditions:

if R is -Λ, R" is hydrogen; if R is hydrogen, R" is -Λ, or R and R" are —$(CH_2)_r$-Λ (for R), where r is an integer from 4 to 12, and -Λ (for R"), respectively, Q being a —$(CH_2)_n$— group where n is an integer from 4 to 12.

What is meant by a straight or branched $C_1$-$C_4$ alkyl group is methyl, ethyl, propyl, isopropyl, n-butyl, sec-butyl, iso-butyl, or ter-butyl.

What is meant by a heterocycle with 5 or 6 members is an aromatic or non-aromatic heterocycle having in the ring at least a heteroatom selected from O, N—$R_1$, or S, such as, for example, 2-, 3- or 4-pyridyl, or 2-, 4-, or 5-imidazolyl.

A first group of preferred compounds according to the invention consists in the formula (I) compounds where R is hydrogen, Q is —$(CH_2)_n$—, where n is an integer from 4 to 8, preferably 6, R" is -Λ, Y is always —$CH_2$—COOH; X is hydrogen, and p is 2.

A further object of the invention described herein consists in formula (I) compounds with radioisotopes for diagnostic and/or therapeutic use. Examples of these isotopes are: Fe-52, Mn-52m, Co-55, Cu-64, Ga-67, Ga-68, Tc-99m, In-111, I-123, I-125, I-131, P-32, Sc-47, Cu-67, Y-90, Pd-109, Ag-111, Pm-149, Re-186, Re-188, At-211, Bi-212, Bi-213, Rh-105, Sm-153, Lu-177, and Au-198.

A first group of preferred complexes according to the invention are those where, in the formula (I) compounds, R is hydrogen, Q is —$(CH_2)_n$—, where n is an integer from 4 to 8, preferably 6, R" is -Λ, Y is always —$CH_2$—COOH; X is hydrogen, p is 2 and the radioisotope is Y-90.

Further objects of the invention described herein are processes for the preparation of formula (I) compounds and their complexes with radiopharmaceuticals.

Further objects of the invention described herein are pharmaceutical and/or diagnostic compositions containing formula (I) compounds and their complexes as indicated above.

Other objects of the invention described herein are the use of formula (I) compounds and their complexes with radioisotopes as medicaments or diagnostic tools, particularly for the preparation of medicaments which are useful in tumour therapy or diagnosis.

These and other objects relating to the invention described herein will be illustrated in detail in the part that follows here below, also by means of experimental examples.

DETAILED DESCRIPTION OF THE INVENTION

The compound according to the invention described herein is prepared according to the following scheme, including the steps of:

a) formation of an amide bond between the carboxyl group of biotin and a primary amine group of $H_2N$-Q-$NH_2$ diamine, the other primary amine group being suitably protected, for example, with a Boc group, if necessary.
b) deprotection of the primary amine group;
c) reduction of the amide group to an amine group;
d) conjugation with the desired formula (II) chelating agent -Λ.

Biotin is a commercial product. $H_2N$-Q-$NH_2$ diamines are available on the market and can in any event be prepared using known methods.

The protection of the primary amine group is easily achieved using known protective groups, such as, for example, Boc, and which in any event can be found in the sales catalogues and in the general literature.

Alternatively, the formula (I) compound according to the invention can be prepared according to the following scheme, if R is hydrogen and R" is a macrocyclic chelating agent -Λ:

a) formation of an amide bond between the carboxyl group of biotin and a primary amine group of $H_2N$-Q-$NH_2$ diamine, the other primary amine group being suitably protected, for example, with a Boc group, if necessary;
b) deprotection of the primary amine group if the protective group is of the alkyl urethane type, sensitive to treatment with $BH_3$.THF, such as, for example, a Boc group;
c) selective protection of said primary amine group with a protective group selected from among those reported in the literature as being resistant to the subsequent reduction and detachable without damaging the biotin ring (T. W. Greene, P. G. M. Wuts, "Protective groups in organic synthesis", 3rd Ed., J. Wiley & Sons, Inc., New York, 1999; Handbook of Reagents for Organic Synthesis, "Oxidizing and Reducing Agents", Edited by S. D. Burke and R. L. Danheiser, J. Wiley & Sons, Inc., New York, 1999);
d) reduction of the amide group to an amine group with $BH_3$.THF;
e) protection of the secondary amine group with protection orthogonal to the preceding protective groups;
f) deprotection of the primary amine group;
g) conjugation with the desired chelating agent as defined above;
h) deprotection of the secondary amine group;
i) or, if R is a macrocyclic chelating agent -Λ and R" is hydrogen, after step d):
j) conjugation with the desired chelating agent -Λ;
k) deprotection of the primary amine group.

The protection of the primary amine group in step a) has already been illustrated above. As regards the protection of the amine group in step c) and the protection of the secondary amine group, the average technician is capable, on the basis of his or her knowledge of the field, of selecting the appropriate protective group.

If R is —$(CH_2)_r$-Λ, and R" is -Λ, the formula (I) compound can be prepared according to the following scheme:

a) activation of the —COOH group of biotin according to the known methods of peptide synthesis (P. Lloyd-Williams, F. Albericio, E. Giralt, "Chemical Approaches to the Synthesis of Peptides and Proteins", CRC Press, Boca Raton, New York, 1997);
b) conjugation of biotin activated with an amine with general formula: BOcNH$(CH_2)_n$NH$(CH_2)_q$NHBoc, where n and q may vary, independently, from 4 to 12;
c) detachment of the protective group Boc;
d) reduction of amide, if desired, that can be performed as above;
e) conjugation with the desired chelating agent -Λ.

A number of secondary amines illustrated in step b) can be obtained on the market; others can be prepared suitably modifying conventional methods (for example see J. B. Hansen, , M. C. Nielsen, U. Ehrbar, O. Buchardt, Synthesis, 1982, 404).

The conjugation of the compound according to the invention with the radioisotope to produce the complexes envisaged in the context of the invention described herein is carried out using the known traditional methods in the field, as described, for example, in Paganelli, Chinol et al. *European Journal of Nuclear Medicine* Vol. 26, No 4; April 1999; 348-357.

DESCRIPTION OF THE PREFERRED EMBODIMENT OF THE INVENTION

There now follows a detailed description of the preparation of the preferred formula (I) compound, that is to say the one in which R is hydrogen, Q is —$(CH_2)_n$—, where n is preferably 6, R" is -A, Y is always —$CH_2$—COOH; X is hydrogen, p is 2.

The process comprises:
- a) formation of an amide bond between the carboxyl group of biotin and the primary amine group of hexamethylenediamine, suitably protected, for example with a Boc group, if necessary;
- b) deprotection of the amine group of hexamethylenediamine;
- c) reduction of the amide group to an amine group;
- d) conjugation with the desired chelating agent.

Step a) in the process according to the invention described herein consists in the formation of an amide bond between the biotin carboxyl group and the primary amine group of hexamethylenediamine-Boc. The biotin was treated with HATU to form an extremely active ester in situ that reacts with the amine group of hexamethylenediamine-Boc to form the relevant amide. This activation mechanism, which is used above all for peptide synthesis in the solid phase, requires a basic medium. To prevent the base from reacting with the active ester, tertiary organic bases such as di-isopropylethylamine (DIPEA) or N-methylmorpholin (NMM) are used. Protection of one of the two amine groups of hexamethylenediamine with Boc (ter-butyloxycarbonyl) is necessary to prevent the biotin binding to both ends of the diamine chain. The end product is isolated from the reaction medium after evaporation of the solvent (DMF) and precipitation with water. The product, recrystallised with propanol, was characterised by $^1$H-NMR, elemental analysis and ESI-MS. The reaction yield is around 88%.

In step b), biotinyl-hexamethylenediamine-Boc is solubilised in a mixture of AcOEt/HCl, approximately 3 M, to detach the Boc group. After removing the solvent mixture the product was lyophilised to completely eliminate HCl. The sample was purified by means of recrystallalisation with an aqueous solution at basic pH and characterised by $^1$H-NMR and TLC.

In step c), the reduction of the amide group was done with $BH_3$.THF. Since the reducing agent is extremely reactive, the process must be carried out in anhydrous conditions. The starting product was held under vacuum prior to the reaction and then solubilised in anhydrous THF (distilled with sodium and benzophenone). The reaction mixture was refluxed in a nitrogen atmosphere until complete reduction of the amide group (as monitored by $^1$H-NMR spectra) had taken place. After evaporating the solvent under reduced pressure, the reaction mixture was treated with an aqueous solution of HCl. After lyophilising the acid solution, the product was purified by recrystallisation from an aqueous solution at basic pH and then by reverse-phase column chromatography. Analysis of the product was done by analytical TLC which revealed its purity. The reaction yield is approximately 55%.

Step d) provides the conjugation reaction of the reduced biotinyl-hexamethylenediamine with DOTA, performed with the specific reagents for the formation of amide bonds in an aqueous medium: 1-(3-dimethylaminopropyl)-3-ethylcarbodiimide hydrochloride (EDC), and sulpho-NHS. DOTA was solubilised in water and adjusted to a pH between $pKa_3$ and $pKa_4$ values in order to activate mostly one of four carboxylic groups. In this way, we can reduce the likelihood of obtaining side products. To the basic solution were added sulpho-NHS and lastly EDC. After the formation of the active ester in situ, the reduced biotinyl-hexamethylenediamine was added, checking that the pH of the solution remained around 8.6. Purification of the crude product was done by semipreparative HPLC ($C_{18}$; $CH_3CN/H_2O$/TFA 0.1%; $CH_3CN$ from 5% to 25% in 20 min).

The objects of the invention described herein are pharmaceutical or diagnostic compositions containing as their active ingredient at least one formula (I) compound, also in the form of a complex with a radioisotope or, in the case of said formula (I) compound, in association with other active ingredients useful in the treatment of the diseases indicated in the invention described herein, e.g. other products possessing anticancer activity; also in separate dosage forms or in forms suitable for combined therapy. The active ingredient according to the invention will be in the form of a mixture along with suitable vehicles and/or excipients commonly used in pharmaceutical technology, such as, for example, those described in "Remington's Pharmaceutical Sciences Handbook", latest edition. The compositions according to the invention shall contain a therapeutically effective amount of the active ingredient. The dosages will be determined by the expert in the field, e.g. the clinician or primary care physician, according to the type of disease to be treated and the patient's condition, or concomitantly with the administration of other active ingredients.

Examples of pharmaceutical compositions are those that allow parenteral or loco-regional administration. Pharmaceutical compositions suitable for the purpose are solutions, suspensions, or lyophilised forms to be reconstituted at the time of use.

Forms suitable for the industrial application of the invention are kits for cancer radiotherapy, as, for example, described in European Patent 0 496 074, in the paper by Paganelli, Chinol et al. published in the *European Journal of Nuclear Medicine* Vol. 26, No 4; April 1999; 348-357, in U.S. Pat. No. 5,968,405 and in the relevant literature.

A further object of the invention described herein is a kit for the therapy or diagnosis of tumours by means of radioactivity. characterised in that at least one of the components of said kit contains a formula (I) compound or one of its complexes with a suitable radioisotope.

The compounds according to the invention are useful for the preparation of therapeutic and/or diagnostic agents for the treatment and diagnosis of tumours.

For example, they can be used in tumour treatment methods with anticancer radiopharmaceuticals, such as, for example, those described in European Patent 0 496 074, in the paper by Paganelli, Chinol et al. published in the *European Journal of Nuclear Medicine* Vol. 26, No 4; April 1999; 348-357, in U.S. Pat. No. 5,968,405 and in the relevant literature.

The following example further illustrates the invention.

EXAMPLE

The NMR spectra were recorded in DMSO-$d_6$ solution.

To a solution of biotin (1 g, 4.1 mmol) and NMM (0.451 ml, 1 eq) in anhydrous DMF was added a solution of N-Boc-hexamethylene-diamine HCl (1.03 g, 1 eq) and NMM (0.451 ml, 1 eq) in anhydrous DMF. After a few minutes a solution of HATU (1.56 g, 1 eq) in DMF was added. The reaction mixture was stirred overnight at room temperature and then evaporated under reduced pressure. The oil thus obtained was crystallised by adding water and recrystallised with n-propanol obtaining 1.6 g (3.6 mmol; 88% yield) of compound 1.

The product was pure by TLC inspection (eluent:DCM/MeOH=5:1; detected by fluorescamine or $Cl_2$/o-tolidine).

Mp: 174-176° C.; $^1$H-NMR, $\delta_H$: 1.1-1.65 [14H, $CH(CH_2)_3$ and $NHCH_2(CH_2)_4$], 1.34 (s, 9 H, tBu), 2.05 (t, 2 H, $CH_2CO$), 2.54 (d, 1 H, HCHS), 2.74-3.15 (6 H, $2\times CH_2N$, HCHS and CHS), 4.12 (m, 1 H, CHCHNH), 4.28 (m, 1 H, $CH_2CHNH$), 6.36 and 6.42 (two s, 2×biotin NH), 6.74 (t, 1 H, Boc NH), 7.74 (t, 1 H, amide NH); ESI-MS: m/e calcd. $[M+H]^+$ 443.1, found 443.1. Elemental analysis: Calcd. for $C_{21}H_{38}N_4O_4S$.$0,5H_2O$: C 55.85; H 8.7; N 12.4. Found: C 56.2; H 8.8; N 12.4.

To a suspension of biotinyl-hexamethylenediamine-Boc (1) (1.6 g) in AcOEt was added 37% aqueous HCl until a solution of approximately 3 M in HCl was obtained. The solution was held under magnetic stirring for 30 min and then evaporated under reduced pressure. The oily product was then lyophilised with water, adjusted to pH 12 with NaOH 2M, and cooled with ice, whereupon the solution was lyophilised once again. The solid obtained (compound 2) was treated several times with MeOH to eliminate the salts present and then purified by precipitation by adding ethyl ether to the methanol solution, obtaining 1.1 g (90% yield) of compound 2. The compound was pure at TLC on silica gel (eluent: n-propanol/AcOH/$H_2O$, 1:1:1) as assessed with a solution of fluorescamine in acetone at 366 nm and with $Cl_2$/o-tolidine.

M.p.: 179-182° C.; $^1$H-NMR, in accordance with compound 1, lacking tBu signal.

To a solution of 8.8 ml of $BH_3$ 1 M in THF, held under a nitrogen atmosphere at 0° C., was added amine 2 (1.5 g, 4.3 mmol) finely powdered and suspended in 15 ml of anhydrous THF. The mixture was held under magnetic stirring at 0° C. for approximately 30 min and then refluxed until the reaction was complete (the progress of the reaction was checked by $^1$H-NMR on aliquots of the reaction mixture treated hot with HCl 3 M and evaporated under reduced pressure). At the end of the reaction HCl 3M was added; the reaction mixture was then refluxed for 3 hours and evaporated under reduced pressure. The crude reaction product (compound 3) was precipitated with water at a pH of approximately 12 and purified by RP-CC (LiChroprep RP-8, 40-63 μm; eluent: $H_2O$/$CH_3CN$/TFA-92:8:0.1) obtaining 1.3 g (2.3 mmol, 55% yield) of compound 3, which was pure at TLC inspection (same process used for compound 2).

$^1$H-NMR, $\delta_H$: 1.30-1.58 [16 H, $CH(CH_2)_4$ and $NHCH_2(CH_2)_4$], 2.53 (d, 1 H, HCHS), 2.82 (7 H, HCHS and $3\times CH_2N$), 3.05 (m, 1 H, CHS), 4.12 (m, 1 H, CHCHNH), 4.28 (m, 1 H, $CH_2CHNH$), 6.38 (br, 2×biotin NH), 8.03 (br, $NH_3^+$), 8.9 (br, $NH_2^+$). ESI-MS: m/e calcd. $[M+H]^+$ 328.23; found 328.2

To a solution of DOTA.$3H_2O$ (100 mg, 0.2 mmol) in water, adjusted to pH 9.2, was added a solution of sulpho-NHS (86.8 mg, 0.4 mmol) in 1 ml of water. After a few minutes a solution of EDC (76.7 mg, 0.4 mmol) in 0.5 ml of water was added dropwise and cooled with ice. The reaction mixture was stirred for approximately 20 min, after which a solution of amine 3 (111 mg, 0.2 mmol) dissolved in 1 ml of water at pH 8.6 was added dropwise. After approximately 3 hours the reaction solution was lyophilised and crude product 4 was purified by reverse phase HPLC ($C_{18}$, A: 0.1% TFA in $CH_3CN$; B: 0.1% TFA in water; from 10 to 15% of B in 20 min; Rt: 12.6 min) obtaining 53 mg (20%) of product, which was pure at TLC (same process used for compound 2). The test with fluorescamine in acetone to ascertain the presence of a primary amine group yielded negative results.

$^1$H NMR, δH: 1.3-1.6 [16 H, $CH(CH_2)_4$ and $NHCH_2(CH_2)_4$], 2.60 (d, 1 H, HCHS), 2.8-2.9 (7 H, HCHS and $3\times CH_2N$), 3.04 (br s, 16 H, $8\times DOTA$-ring $CH_2$), 3.11 (m, 1H, CHS), 3.61 (br s, 8 H, $4\times DOTA$ $CH_2CO$), 4.15 (m, 1 H, CHCHNH), 4.33 (m, 1 H, $CH_2CHNH$), 6.40 and 6.44 (two s, 2×biotin NH), 8.27 (br, amide NH), 8.54 (br, $NH_2^+$). FAB-MS: [M+H]+ calcd. 715.9; found 715.6.; ESI-MS: [M+H]+ found 715,4. Elemental analysis. Calcd. for $C_{32}H_{58}N_8O_8S$.4TFA.$H_2O$: C, 40.41; H, 5.43; N, 9.42. Found: C, 40.48; H, 5.45; N, 9.09.

Labelling tests, avidin binding tests, and serum stability tests were carried out with the compound illustrated in the foregoing example.

Binding Studies.

Avidin was reacted with $^{90}$Y-DOTA-biotin at increasing amounts of labelled biotin. The presence of other radioactive peaks besides that of the avidin-biotin complex was checked by FPLC using the isocratic conditions above described. The radiopeak corresponding to the $^{90}$Y-DOTA-biotin/avidin complex showed a retention time of 9 ml whereas the peak of the unbound $^{90}$Y-DOTA-biotin eluted at 15 min.

The results of the affinity studies between avidin and the $^{90}$Y labelled biotin derivative of Example 1 at the natural 1:4 molar ratio and in molar excess of avidin (1:2) are summarized in Table 1.

TABLE 1

| Molar ratios avidin/biotin-DOTA | | |
|---|---|---|
| Avi:Biot. Molar ratio | 1:2 | 1:4 |
| $^{90}$Y-DOTA-Biotin (μg) | 1 | 2 |
| Avidin (μg) | 51 | 51 |
| Binding (%) | 99.8 | 99.7 |

Beginning with molar excess of avidin, only one peak in the radiochromatogram, corresponding to the avidin-biotin complex, was observed. The same FPLC profile was obtained with a two fold increased amount of $^{90}$Y-DOTA-biotin demonstrating that the natural affinity of the system was maintained.

Affinity Studies.

The displacement of $^{90}$Y-DOTA-biotin from avidin by the action of natural biotin (vitamin-H), starting from a ratio of 1:4 avidin:biotin was studied. The complete binding at 1:4 avidin:biotin molar ratio was initially checked by size exclusion FPLC using the above mentioned conditions. Aliquots from this solution were added with increasing molar amounts of vitamin-H and after 15 min. of incubation at room temperature each of them was analyzed by FPLC. The extent of displacement was calculated by the reduction of avidin-biotin radiopeak compared to the rising of the displaced $^{90}$Y-DOTA-biotin radiopeak. The results are summarized in Table 2

TABLE 2

| Affinity studies with biotin. | | | | | |
|---|---|---|---|---|---|
| Avi:Vit. H Molar ratio | 1:2 | 1:4 | 1:8 | 1:16 | 1:32 |
| $^{90}$Y-DOTA-Biotin (µg) | 0.25 | 0.25 | 0.25 | 0.25 | 0.25 |
| Coupled Avidin (µg) | 6.4 | 6.4 | 6.4 | 6.4 | 6.4 |
| Added Biotin (µg) | 0.047 | 0.094 | 0.188 | 0.376 | 0.752 |
| Displacement (%) | 0.2 | 0.0 | 0.8 | 0.0 | 0.0 |

The results <1% were considered beneath the experimental error.

It can be seen that even a large molar excess of vitamin-H could not displace the $^{90}$Y-DOTA-biotin already bound to avidin.

Stability Studies.

50 µl of the labelling mixture, corresponding to 1.85 MBq of $^{90}$Y were diluted 20 fold with saline or human serum and incubated at 37° C. Solution were analyzed at different time points, up to 144 hours after labelling. To perform the analysis, an aliquot of the incubation mixture was added to a molar excess of avidin. The $^{90}$DOTA-biotin/avidin complex ratio vs. free $^{90}$Y, was determined by FPLC as above described.

The stability studies showed that in saline, the radiolabel was still completely associated with the avidin-biotin complex up to 144 h.

In serum, only one radiopeak was initially detected in the chromatograms of the samples incubated up 48 h, however, afterwards a steady dissociation of $^{90}$Y from DOTA-biotin was observed reaching a maximum of 55% at 144 h.

Beginning in the sample incubated 72 h, a second peak at lower retention time (8.2 min.) was observed in the radiochromatogram indicating that the $^{90}$Y activity was associated with an high molecular weight species, presumably serum transferrin.

The invention claimed is:

1. A compound of Formula (I):

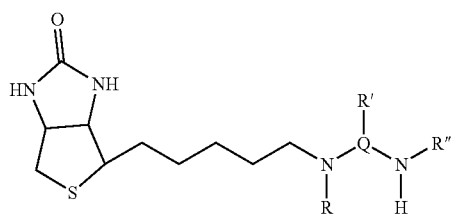

(I)

where:

Q is a —$(CH_2)_n$— group, where n is an integer from 4 to 12, in which case R' does not exist, or Q is selected from the group consisting of —$(CH_2)_a$—CH(R')—$(CH_2)_b$—, where a and b are, independently, 0 or h, wherein h is an integer from 4 to 12, R' is as defined here below, or Q is cyclohexyl, phenyl, in which case R' is a substituent on the cyclohexyl or phenyl ring;

R is hydrogen or -Λ, where -Λ is a formula (II) macrocycle:

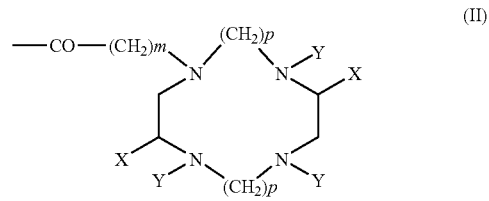

(II)

where the various Ys, which may be the same or different, are selected from the group consisting of hydrogen, a $C_2$ alkyl group, straight or branched $C_3$-$C_4$ alkyl, —$(CH_2)_m$—COOH, where m is an integer from 1 to 3;

X is hydrogen, or the —$CH_2$—U group, where U is selected from methyl, ethyl, p-aminophenyl, or X is the —$(CHW)_o$—Z group, where o is an integer from 1 to 5, W is hydrogen, methyl or ethyl, Z is a heterocyclic group with 5 or 6 members containing one or more heteroatoms selected from O, N—$R_1$, $R_1$ being a hydrogen, $C_1$-$C_2$ alkyl group, or a straight or branched $C_3$-$C_4$ alkyl group, and S; or Z is selected from —$NH_2$, —NH—C(=NH)—$NH_2$, or —S—$R_2$ where $R_2$ is a $C_1$ or $C_2$ alkyl group or a straight or branched $C_3$-$C_4$ alkyl group;

p is the integer 2 or 3

R' is selected from the group consisting of hydrogen, a $C_1$-$C_2$ alkyl group, a straight or branched $C_3$-$C_4$ alkyl, —$(CH_2)_q$—T, where T is selected from the group consisting of S—$CH_3$, —OH, or —COOH, and q is the integer 1 or 2;

R" has the same meanings as R, with the following conditions:

if R is -Λ, R" is hydrogen; if R is hydrogen, R" is -Λ, or R and R" are $(CH_2)_r$-Λ (for R), where r is an integer from 4 to 12, and -Λ (for R"), respectively, Q being a —$(CH_2)_n$— group where n is an integer from 4 to 12.

2. A composition containing a compound according to claim 1, in a mixture with a suitable vehicle and/or excipient.

* * * * *